United States Patent
Kii (10) Patent No.: US 9,927,605 B2
(45) Date of Patent: Mar. 27, 2018

(54) TIME LAPSE SHOOTING APPARATUS AND OBSERVATION METHOD

(75) Inventor: Hiroaki Kii, Kawasaki (JP)

(73) Assignee: NIKON CORPORATION, Tokyo (JP)

( * ) Notice: Subject to any disclaimer, the term of this patent is extended or adjusted under 35 U.S.C. 154(b) by 55 days.

(21) Appl. No.: 13/565,281

(22) Filed: Aug. 2, 2012

(65) Prior Publication Data

US 2012/0327210 A1  Dec. 27, 2012

Related U.S. Application Data

(63) Continuation of application No. PCT/JP2011/000468, filed on Jan. 28, 2011.

(30) Foreign Application Priority Data

Feb. 3, 2010  (JP) .................................. 2010-022170

(51) Int. Cl.
*H04N 7/18* (2006.01)
*G02B 21/36* (2006.01)
*G01N 21/64* (2006.01)

(52) U.S. Cl.
CPC ....... *G02B 21/367* (2013.01); *G01N 21/6408* (2013.01); *G01N 21/6458* (2013.01)

(58) Field of Classification Search
CPC ............. G02B 21/367; G01N 21/6458; G01N 21/6408; C12M 23/50; C03B 5/16
USPC ...... 348/79; 250/459.1; 359/395; 435/303.1; 506/38
See application file for complete search history.

(56) References Cited

U.S. PATENT DOCUMENTS 4,301,252 A * 11/1981 Baker et al. ................ 435/303.1
6,724,419 B1 * 4/2004 Green ................... G02B 21/367
                                                          348/79
2004/0183921 A1  9/2004 Ueda
2005/0282268 A1  12/2005 Kagayama
(Continued)

FOREIGN PATENT DOCUMENTS

EP  1764640 A2  3/2007
JP  2004-309719  11/2004
(Continued)

OTHER PUBLICATIONS

Extended European Search Report dated Jun. 18, 2013 in corresponding European Application No. 11739532.7.
(Continued)

*Primary Examiner* — Mohammed Rahaman
*Assistant Examiner* — Richard Carter (57) ABSTRACT

A certain material irregularly expressed in an observation area is effectively observed. An observing apparatus includes a first observing unit performing a time lapse shooting of a predetermined observation area, a first discriminating unit discriminating whether or not a first material is expressed in the observation area based on an image obtained by the first observing unit, and a second observing unit starting a time lapse shooting relating to a part where the first material is expressed at a timing when the first material is expressed in the observation area, in which a shooting frequency of the time lapse shooting by the second observing unit is higher than a shooting frequency of the time lapse shooting by the first observing unit.

15 Claims, 6 Drawing Sheets

(56) References Cited

U.S. PATENT DOCUMENTS

| | | | |
|---|---|---|---|
| 2006/0176367 A1* | 8/2006 | Endo | G02B 21/367 348/79 |
| 2007/0064101 A1* | 3/2007 | Hasegawa | G02B 21/367 348/79 |
| 2007/0085024 A1* | 4/2007 | Kinoshita | C03B 5/16 250/459.1 |
| 2008/0247038 A1* | 10/2008 | Sasaki et al. | 359/395 |
| 2009/0274360 A1 | 11/2009 | Suzuki et al. | |
| 2009/0322870 A1* | 12/2009 | Fujiki | 348/79 |
| 2010/0157423 A1* | 6/2010 | Houjou | C12M 23/50 359/395 |
| 2010/0214404 A1* | 8/2010 | Chen et al. | 348/79 |
| 2012/0220498 A1* | 8/2012 | Takahashi et al. | 506/38 |

FOREIGN PATENT DOCUMENTS

| | | |
|---|---|---|
| JP | 2006-350004 | 12/2006 |
| JP | 2007-108154 | 4/2007 |
| JP | 2011-2254 | 1/2011 |
| WO | WO 2006/106882 | 10/2006 |

OTHER PUBLICATIONS

Jérôme Artus et al., "Live Imagine Genetically-Encoded Fluorescent Proteins in Embryonic Stem Cells Using Confocal Microscopy", Modern Research and Educational Topics in Microscopy, 2007, pp. 190-202.

International Preliminary Report on Patentability dated Aug. 16, 2012 (English Translation dated Sep. 27, 2012) in corresponding International Patent Application No. PCT/JP2011/000468.

International Search Report of Corresponding PCT Application PCT/JP2011/000468 dated May 10, 2011.

Office Action issued by the European Patent Office dated Apr. 20, 2017 in corresponding European patent application No. 11 739 532.7.

* cited by examiner

TIME LAPSE SHOOTING APPARATUS AND OBSERVATION METHOD

CROSS REFERENCE TO THE RELATED APPLICATION

This application is a continuation application of International Application PCT/JP2011/000468, filed Jan. 28, 2011, designating the U.S., and claims the benefit of priority from Japanese Patent Application No. 2010-022170, filed on Feb. 3, 2010, the entire contents of which are incorporated herein by reference.

BACKGROUND

1. Field

The present application relates to an observing apparatus performing a time lapse shooting of an observation object such as a living sample and an observation method.

2. Description of the Related Art

Conventionally, a living sample observing apparatus performing a time lapse shooting while incubating cells in an incubation container is known in Japanese Unexamined Patent Application Publication No. 2004-309719.

On the other hand, in recent years, an art manufacturing, differentiating and inducing iPS cells (Induced Pluripotent Stem cell) from cultured cells differentiated into somatic cells is focused and various studies have been done in various fields such as a regenerative medicine field and a development of new drugs field.

As a representative method manufacturing the iPS cells from the cultured cells, a method in which an exogenous gene called as Yamanaka factors (Sox 2, K1f4, Oct3/4, c-Myc) is introduced into the cultured cells with a vector such as retrovirus and plasmid, and they are incubated for several weeks is known. The cells to which the exogenous gene is introduced are reprogrammed (initialized) and come to have equivalent characteristics as ES cells (a characteristic multiplying in a colony state mode, and having pluripotency) in various points. In the cells initialized as stated above, an endogenous gene peculiar to the iPS cells such as a Nanog gene is expressed. Besides, the expression of the introduced exogenous gene is terminated simultaneously with the initialization of cells caused by a mechanism called as a silencing in the cell.

In this method, it becomes important to monitor a process from the expression of the exogenous gene to the termination of the expression thereof caused by the silencing (1) and a process in which the endogenous gene peculiar to the iPS cells is expressed by the initialization (2) from points of view of an evaluation, an explanation of function of the iPS cells.

It is possible to visualize these processes (1) and (2), and for example, when the process (1) is visualized, a fluorescent protein gene (DsRed gene) which is expressed together with the expression of the above-stated exogenous gene (Sox2, K1 f4, Oct 3/4, c-Myc) and silencing thereof occurs together with the exogenous gene is introduced into the cultured cells together with the exogenous gene. Besides, when the process (2) is visualized, the endogenous gene (Nanog gene) in experimental animals is recomposed into a gene accompanied by the fluorescent protein (Nanog-GFP gene) in advance.

However, manufacturing efficiency of the iPS cells is currently low, and therefore, the iPS cells are not expressed only at a very small part in the incubation container. Besides, it is currently impossible to predict a part where the iPS cells are expressed. Accordingly, it is difficult to effectively observe the processes (1) and (2) in which the iPS cells are initialized with the above-stated living sample observing apparatus.

A proposition of the present application is to provide an observing apparatus and an observation method capable of effectively observe a certain material which is irregularly expressed in an observation area.

SUMMARY

An observing apparatus exemplifying the present embodiment includes a first observing unit performing a time lapse shooting of a predetermined observation area, a first discriminating unit discriminating whether or not a first material is expressed in the observation area based on an image obtained by the first observing unit, and a second observing unit starting a time lapse shooting relating to a part where the first material is expressed at a timing when the first material is expressed in the observation area, in which a shooting frequency of the time lapse shooting by the second observing unit is higher than a shooting frequency of the time lapse shooting by the first observing unit.

An observation method exemplifying the present embodiment includes a first observing step performing a time lapse shooting of a predetermined observation area, a first discriminating step discriminating whether or not a first material is expressed in the observation area based on an image obtained at the first observing step, and a second observing step starting a time lapse shooting relating to a part where the first material is expressed at a timing when the first material is expressed in the observation area, in which a shooting frequency of the time lapse shooting by the second observing step is higher than a shooting frequency of the time lapse shooting by the first observing step.

According to the present application, an observing apparatus and an observation method capable of effectively observe a certain material which is irregularly expressed in an observation area are enabled.

DETAILED DESCRIPTION OF THE EMBODIMENT

Embodiment

Hereinafter, a living sample observing apparatus is described as an embodiment of the present invention.

Figure 1:
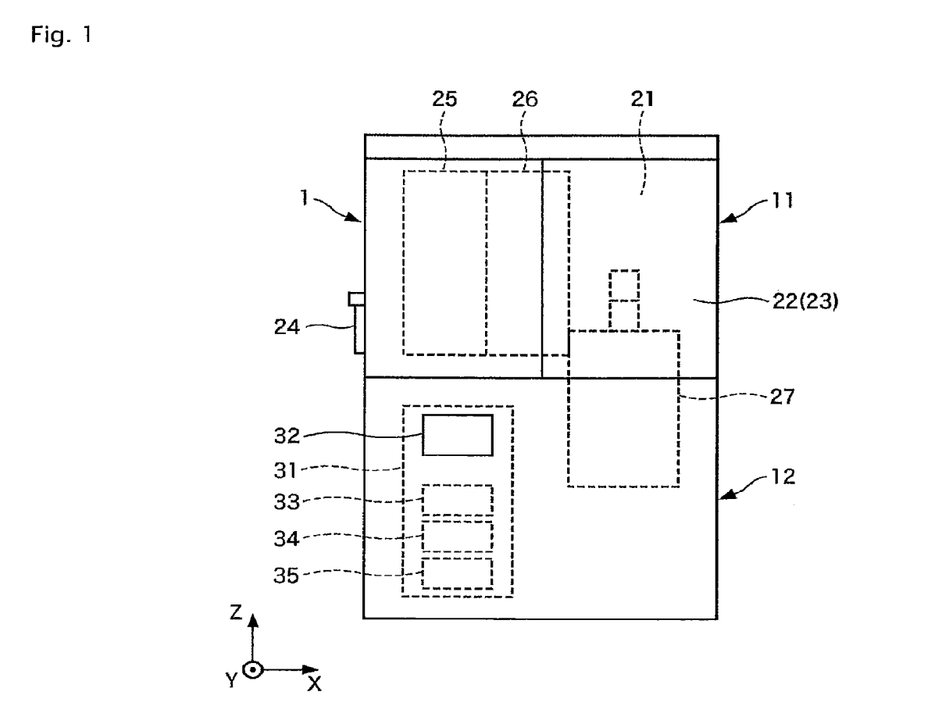
FIG. 1 is a front view illustrating an overall configuration of a living sample observing apparatus.

FIG. 1 is a front view illustrating an overall configuration of the living sample observing apparatus. Note that in FIG. 1, a solid line illustrates a structure of a portion exposed to an external appearance, and a dotted line illustrates a structure of an internal portion which is not exposed to the external appearance.

As illustrated in FIG. 1, a living sample observing apparatus 1 includes a first casing 11 housing incubation containers accommodating cells and a second casing 12 making up a controlling apparatus. The first casing 11 is used under a state mounted on the second casing 12.

A temperature-controlled room 21 covered with a heat insulating material is formed inside the first casing 11. This temperature-controlled room 21 is communicated with outside by a front opening 23 (front door 22) formed at a front face of the first casing 11 and a carry-in entrance 24 formed at a left side surface when it is seen from the front of the first casing 11.

For example, a temperature controlling mechanism made up of a temperature adjusting apparatus and so on in which Peltier element is used, a humidity controlling mechanism made up of an atomizer and so on spraying mist, a gas controlling mechanism made up of a gas introducing section and so on coupled to an external carbon dioxide cylinder, an environmental sensor detecting an environment of the incubation container in an internal space (all of them are not illustrated) and so on are provided at the temperature-controlled room 21. Inside of the temperature-controlled room 21 is thereby sealed to maintain the environment of the incubation container, and for example, it is kept at a constant temperature by circulating air, and thereby, it is maintained at a temperature of 37° C., a humidity of 90%, and a carbon dioxide concentration of 5%, and so on.

Besides, a stocker 25, a container transfer mechanism 26 and an observing unit 27 are housed in the temperature-controlled room 21 of the first casing 11.

The stocker 25 is divided into up and down parts by plural shelves, and the incubation container 15 (FIG. 2, FIG. 3) can be horizontally housed.

A transfer arm section supporting a holder and various mechanisms (not-illustrated) to transfer the incubation container 15 are provided at the container transfer mechanism 26. The container transfer mechanism 26 is able to transfer the holder supported by the transfer arm section in a vertical direction (Z direction) or a horizontal direction (X and Y directions), and to rotate the holder for 180 degrees centering on a Z axis.

Figure 2:
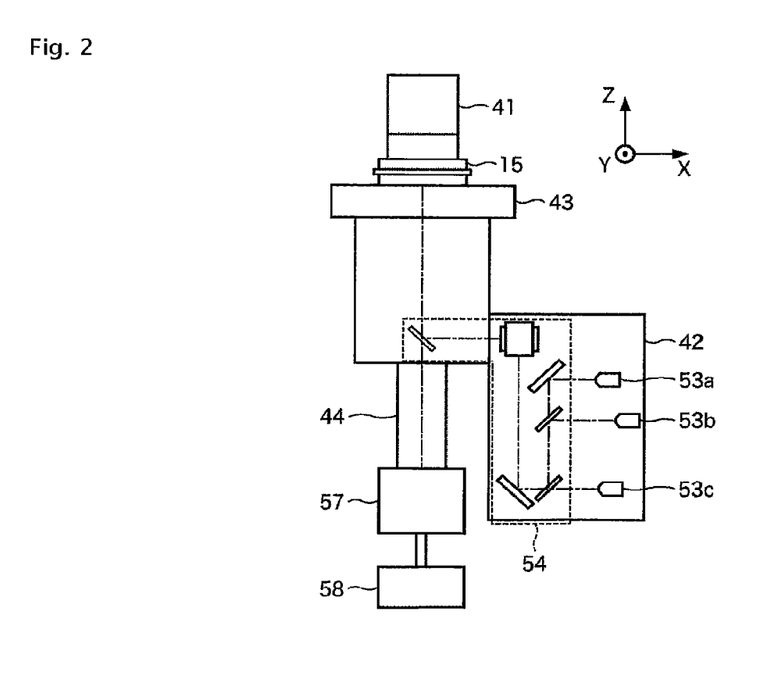
FIG. 2 is a front view of an observing unit 27.
Figure 3:
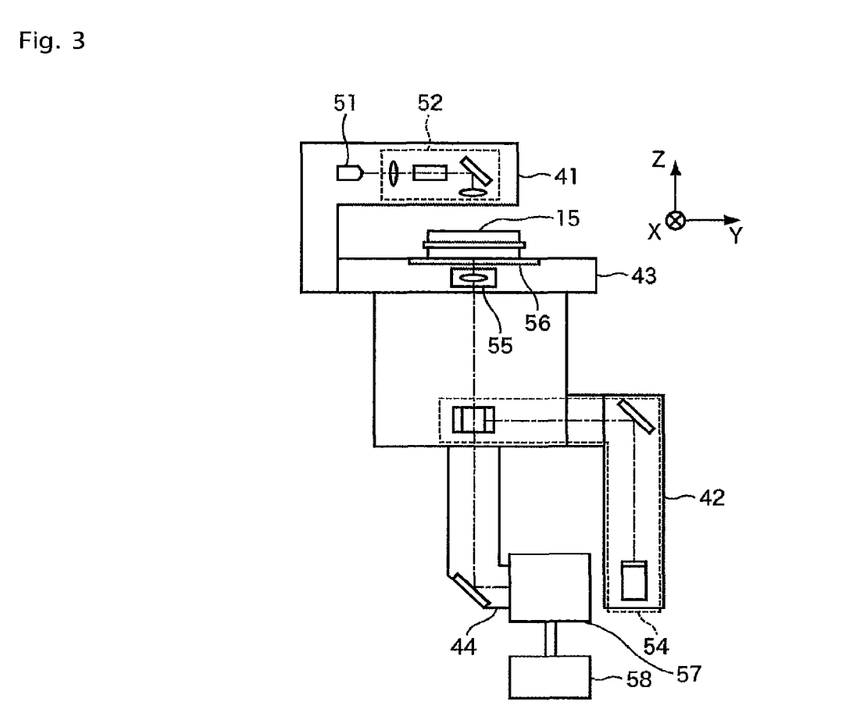
FIG. 3 is a side view of the observing unit 27.

FIG. 2 and FIG. 3 are views illustrating a configuration of the observing unit 27. A front view of the observing unit 27 is illustrated in FIG. 2, and a side view of the observing unit 27 is illustrated in FIG. 3.

As illustrated in FIG. 2 and FIG. 3, the observing unit 27 is made up of a diascopic illuminating section 41, a fluorescence epi-illuminating section 42, a sample stage 43 and an observing section 44.

The diascopic illuminating section 41 is formed in an arm state extending from a side part of the sample stage 43 toward an upper direction, and thereafter, extending to an upper part of the incubation container 15 placed on the sample stage 43. An LED (Light Emitting Diode) for diascopic illumination 51 and an optical system for diascopic illumination 52 are housed in the diascopic illuminating section 41. The LED for diascopic illumination 51 emits light at a predetermined wavelength region. The light from the LED for diascopic illumination 51 is irradiated on the incubation container 15 placed on the sample stage 43 via the optical system for diascopic illumination 52 from an upper side. Note that an illumination (diascopic illumination) by means of the diascopic illuminating section 41 is desirable to be an illumination (dark-field illumination and so on) suitable for visualizing the transparent incubation container 15 and a transparent phase substance (cells and so on) existing in the incubation container 15.

The fluorescence epi-illuminating section 42 includes LEDs for fluorescence 53a, 53b, 53c and an optical system for fluorescence 54. The LEDs for fluorescence 53a, 53b, 53c emit lights at different wavelengths from one another. The lights emitted from the LEDs for fluorescence 53a, 53b, 53c are irradiated on the sample stage 43 via the optical system for fluorescence 54 from a lower side.

The sample stage 43 is made up of a transparent material, and the light emitted from the diascopic illuminating section 41 and transmitting the incubation container 15, and fluorescence emitted at the incubation container 15 in accordance with excitation light emitted from the fluorescence epi-illuminating section 42 are seldom interrupted and incident on the observing section 44.

An objective lens 55 condensing the light heading from the incubation container 15 to the observing section 44, a stage 56 transferring the incubation container 15 in the vertical direction or the horizontal direction and so on are also provided at the sample stage 43.

The objective lens 55 at the sample stage 43 is made up of plural objective lenses of which magnifications are different (for example, a two times objective lens, a four times objective lens, a 10 times objective lens, a 20 times objective lens, a 40 times objective lens, and so on), and an observation magnification of the observing unit 27 can be switched appropriately.

The observing section 44 is made up of a shooting section 57 and an image processing section 58. The shooting section 57 includes an image-forming optical system and an imaging device such as a CCD (Charge Coupled Device). The image-forming optical system of the observing section 44 forms an image (diascopic image) by the light transmitting the incubation container 15 and an image (fluorescence image) by the fluorescence emitted from the incubation container 15 on an imaging area of the imaging device.

Here, the optical system for fluorescence 54 is able to switch kinds of light irradiating the incubation container 15 (illumination methods of the observing unit 27) between the illumination by the fluorescence epi-illuminating section 42 (epi-illumination) and the illumination by the diascopic illuminating section 41 (diascopic illumination) by inserting/detaching a dichroic mirror disposed at a predetermined position inside the optical system for fluorescence 54.

For example, the shooting section 57 is able to obtain a diascopic image of the incubation container 15 under a state in which the illumination method of the observing unit 27 is set to the diascopic illumination, and only the LED for diascopic illumination 51 is lighted from among the above-stated four LEDs.

Besides, the shooting section 57 is able to obtain a fluorescence image of the incubation container 15 under a state in which the illumination method of the observing unit 27 is set to the epi-illumination, and any one of the LEDs for fluorescence 53a, 53b, 53c is lighted from among the above-stated four LEDs.

Besides, a wavelength (an excitation wavelength of the observing unit 27) of light irradiating the incubation container 15 is switched when the lighting LED changes among the three LEDs for fluorescence 53a, 53b, 53c under the state in which the illumination method of the observing unit 27 is set to the epi-illumination.

Further, a wavelength band (a detection channel of the observing unit 27) capable of being incident on the shooting section 57 is switched when a fluorescence filter disposed at a predetermined position in the optical system for fluorescence 54 is switched under the state in which the illumination method of the observing unit 27 is set to the epi-illumination.

The image processing section 58 applies an analog signal process including an amplifying process and so on for an image (analog image signal) obtained by the shooting section 57, and thereafter, performs an A/D (Analog/Digital) conversion of the analog image signal to obtain a digital image signal. This digital image signal is transmitted to a controlling unit 31.

Returning to FIG. 1, the controlling unit 31 is also housed in addition to a part of the above-stated observing unit 27 in the second casing 12 on which the first casing 11 is placed.

The controlling unit 31 controls operations of each section of the living sample observing apparatus 1. Specifically, the controlling unit 31 performs an adjustment of environmental conditions in the temperature-controlled room 21, carrying in/out of the incubation container 15 to/from the temperature-controlled room 21, an observation of the living sample in the incubation container 15, a transfer of the incubation container 15 in the temperature-controlled room 21, and so on in accordance with an observation schedule or a direct instruction by an operation of a user.

Besides, the controlling unit 31 displays necessary information on a display panel 32 provided at a front surface and so on of the second casing 12, and thereby, it is possible to make the user input the observation schedule by each incubation container. Note that the information input from the user to the controlling unit 31 is performed via an input device (not-illustrated) such as a keyboard coupled to the controlling unit 31.

Further, an observation information storing section 33 is provided in the controlling unit 31, and the observation information storing section 33 sequentially stores the digital image signals supplied from the observing unit 27. The image data of plural images (hereinafter, referred to just as the "image") are thereby accumulated at the observation information storing section 33.

Besides, the controlling unit 31 adds index information such as a number (container number) of the incubation container 15 which is an obtaining original of the image and an obtaining time and date of the image for individual images to manage the plural images accumulated at the observation information storing section 33 by each incubation container and by each time and date. Further the observation information storing section 33 is able to record a change history and so on of the environmental conditions (temperature, humidity, carbon dioxide concentration and so on) in the temperature-controlled room 21.

An image analyzing section 34 performs an image analyzing process for the images accumulated at the observation information storing section 33 according to need.

An observation controlling section 35 controls the observing unit 27 in accordance with the observation schedule or the direct instruction by the user's operation. Besides, the observation controlling section 35 appropriately changes control contents of the observing unit 27 based on a result of the image analyzing process by the image analyzing section 34.

Note that the controlling unit 31 includes a communication unit (not-illustrated) based on a predetermined wireless or wired communication protocol, and it is possible to perform data transmission/reception with equipments such as external personal computers via a network. Accordingly, the user is able to perform the observation of the incubation container, a setting change of the observing unit 27, a setting change of the temperature-controlled room 21 from a computer located at a remote location.

Figure 4:
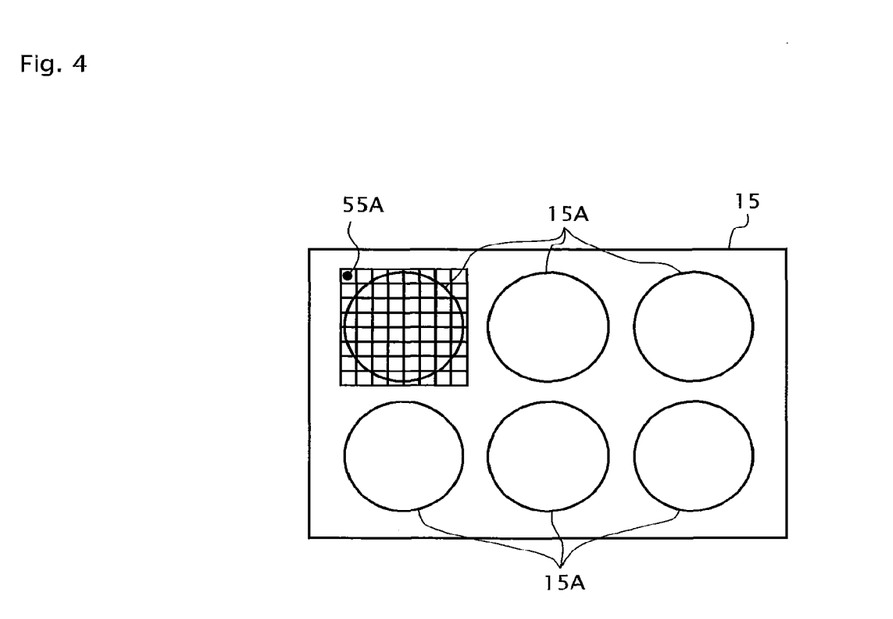
FIG. 4 is an upper surface view of an incubation container 15 (well plate).

Here, in the present embodiment, a well plate as illustrated in FIG. 4 is assumed as the incubation container 15. The number of wells of the incubation container 15 is, for example, six pieces, and a diameter of each well 15A is approximately 30 mm. Various elements required for manufacturing of the iPS cells, namely, a culture solution, feeder cells, cultured cells differentiated into somatic cells (mouse fibroblast), a vector to introduce Yamanaka factors into the cultured cells, and so on are housed at proper timings in each well 15A. In particular, processes (introduction of a DsRed gene, genetic recombination from a Nanog gene to a Nanog-GFP gene) to visualize the above-stated processes (1), (2) are performed for the cultured cells in advance.

When the objective lens 55 of the observing unit 27 is set to be the two times objective lens, a size of a range (a visual field 55A of the observing unit 27) capable of being imaged by one shot within the incubation container 15 is, for example, 4 mm×4 mm. Accordingly, the imagings for 8×8 shots are performed while moving the visual field 55A of the observing unit 27 on the incubation container 15, and the obtained images of 8×8=64 pieces are connected (tiling) to observe almost a whole of one well 15A as illustrated by a grid line in FIG. 4.

Besides, when the objective lens 55 of the observing unit 27 is set to be the 20 times objective lens, a size of a range (the visual field of the observing unit 27) capable of being imaged by one shot within the incubation container 15 is, for example, 400 μm×400 μm. This size is suitable to observe one cell colony generated in the incubation container 15 in detail.

Besides, an emission wavelength of the LED for fluorescence 53a of the observing unit 27 of the present embodiment is set at an excitation wavelength (558 nm) of the DsRed, and an emission wavelength of the LED for fluorescence 53b is set at an excitation wavelength (488 nm) of the Nanog-GFP. In this case, the excitation wavelength of the observing unit 27 is able to be switched between the excitation wavelength (558 nm) of the DsRed and the excitation wavelength (488 nm) of the Nanog-GFP.

Further, the detection channel of the observing unit 27 is able to be switched between a fluorescence wavelength band (in a vicinity of 583 nm. Hereinafter, referred to as a "red color channel") of the DsRed and a fluorescence wavelength band (in a vicinity of 520 nm. Hereinafter, referred to as a "green color channel") of the Nanog-GFP.

In this case, it is possible to obtain a fluorescence intensity distribution of the DsRed (DsRed image) existing in the incubation container 15 when the illumination method of the observing unit 27 is set to the epi-illumination, the excitation wavelength of the observing unit 27 is set at 558 nm, and the detection channel of the observing unit 27 is set at the red color channel.

Besides, it is possible to obtain a fluorescence intensity distribution of the Nanog-GFP (GFP image) existing in the incubation container 15 when the illumination method of the observing unit 27 is set to the epi-illumination, the excitation wavelength of the observing unit 27 is set at 488 nm, and the detection channel of the observing unit 27 is set at the green color channel.

Figure 5:
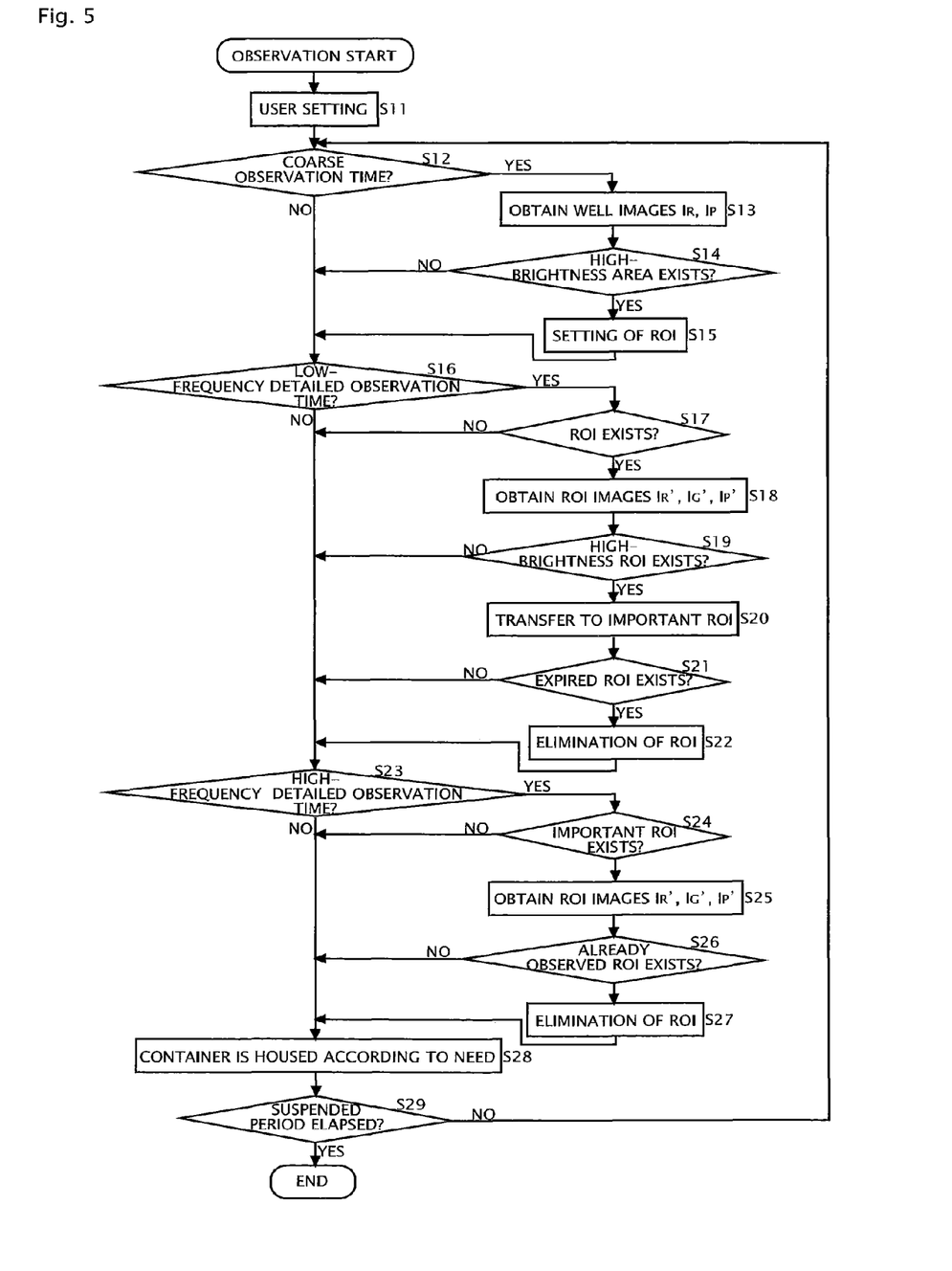
FIG. 5 is a flowchart of an observation process by a controlling unit 31.

FIG. 5 is a flowchart of an observation process by the controlling unit 31. Hereinafter, respective steps are sequentially described. Note that it is assumed that the above-stated incubation container 15 is already housed in the living sample observing apparatus (the container number is assigned and housed in the stocker 25) at a starting time of the flow.

Step S11: The controlling unit 31 makes the user input the observation schedule of the incubation container 15. Here, there are a time lapse shooting of which interval is long (coarse observation), a time lapse shooting of which interval is short (low-frequency detailed observation) and a time lapse shooting of which interval is further short (high-frequency detailed observation) in the observation process of the present embodiment. Accordingly, the controlling unit 31 of this step makes the user set each of an interval $\Delta T1$ of the coarse observation, an interval $\Delta T2$ of the low-frequency detailed observation and an interval $\Delta T3$ of the high-frequency detailed observation. The user sets a combination of the intervals $\Delta T1$, $\Delta T2$, $\Delta T3$ to be a combination satisfying a relationship as described below.

$$\Delta T3 < \Delta T2 < \Delta T1$$

$$\Delta T2 = n \times \Delta T3 \text{ (where ``}n\text{'' is an integer)}$$

$$\Delta T1 = m \times \Delta T2 \text{ (where ``}m\text{'' is an integer)}$$

Accordingly, for example, they are set as $\Delta T1=8$ h, $\Delta T2=2$ h, $\Delta T3=1$ h, and so on.

Note that a necessary time per one round of each of the coarse observation, the low-frequency detailed observation, the high-frequency detailed observation are enough shorter compared to these intervals $\Delta T1$, $\Delta T2$, $\Delta T3$, and therefore, they are regarded as zero in this description.

Besides, the controlling unit 31 makes the user set each of a brightness threshold value A1 to detect presence/absence of expression of the DsRed and a brightness threshold value A2 to detect presence/absence of expression of the Nanog-GFP. The user sets the brightness threshold value A1 to be low when it is necessary to detect the presence/absence of the expression of the DsRed with high sensitivity, and sets the brightness threshold value A2 to be low when it is necessary to detect the presence/absence of the expression of the Nanot-GFP with high sensitivity (incidentally, a necessity to set the brightness threshold value A2 lower than the brightness threshold value A1 is generally high).

Further, the controlling unit 31 makes the user set a magnification $m_L$ of the objective lens to be used for the coarse observation. Hereinafter, the magnification $m_L$ is assumed to be set at "2".

The controlling unit 31 calculates a shot pattern $P_L$ (a moving pattern of the stage 56 and a drive timing of the shooting section 57) necessary for imaging all wells of the incubation container 15 in the coarse observation in accordance with the set magnification $m_L$. Note that here, the magnification $m_L$ is set at "2", and therefore, a shot pattern imaging one well with 8×8 shots as illustrated in FIG. 4 is calculated as the shot pattern $P_L$.

Besides, the controlling unit 31 makes the user set a magnification $m_H$ of the objective lens and a size $S_{ROI}$ of a ROI to be used for the low-frequency detailed observation. Note that the ROI is an area to be an object of the low-frequency detailed observation. Hereinafter, it is assumed that the magnification $m_H$ is set at "20", and the size $S_{ROI}$ is set at a size of "300 μm×300 μm" corresponding to one cell colony.

The controlling unit 31 calculates a shot pattern $P_H$ necessary for imaging for one ROI with the low-frequency detailed observation in accordance with a combination of the set magnification $m_H$ and the size $S_{ROI}$. Note that, here, the magnification $m_H$ is set at "20", and the size $S_{ROI}$ is set at "300 μm×300 μm", and therefore, a shot pattern imaging one ROI by one shot is calculated as the shot pattern $P_H$.

Figure 7A:
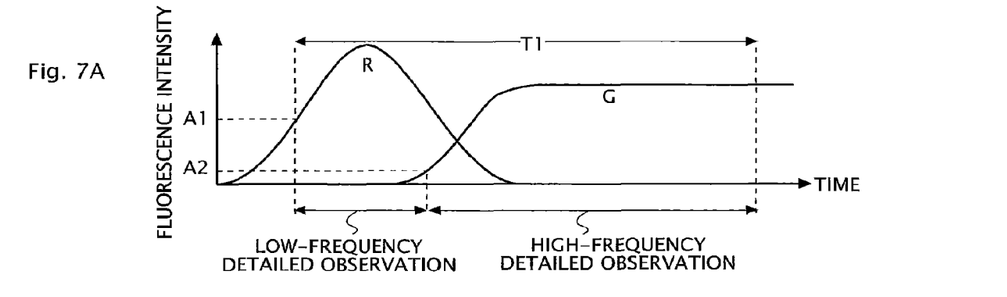
FIGS. 7A to 7D are views explaining a relationship between a time change of fluorescence intensities of plural cell colonies different from one another and a detailed observation period T1 and a suspended period T2.
Figure 7B:
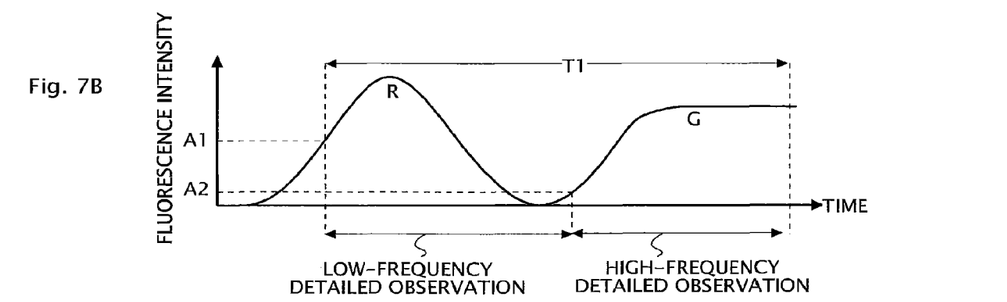
Figure 7C:
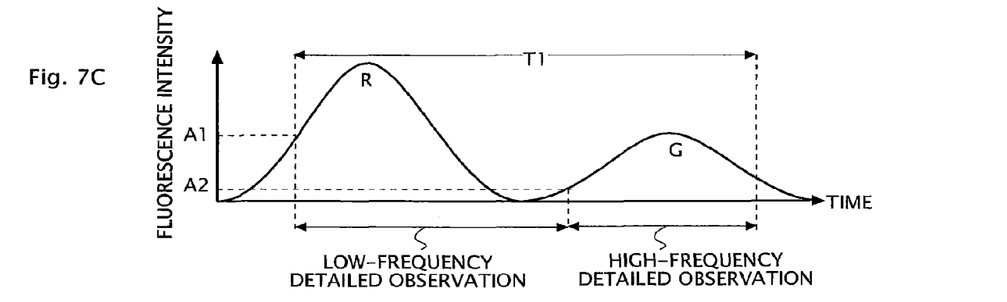

Besides, the controlling unit 31 makes the user set a period (detailed observation period) T1 in which the low-frequency detailed observation and the high-frequency detailed observation are to be continued. The detailed observation period T1 is set to be a period necessary from the time when the DsRed is expressed at the cell colony, then the Nanog-GFP is expressed, and thereafter, to the time when it is verified whether or not the cell colony becomes the iPS cell colony as illustrated in FIGS. 7A to 7C. For example, the detailed observation period T1 is set to be 504 h (three weeks).

Figure 7D:
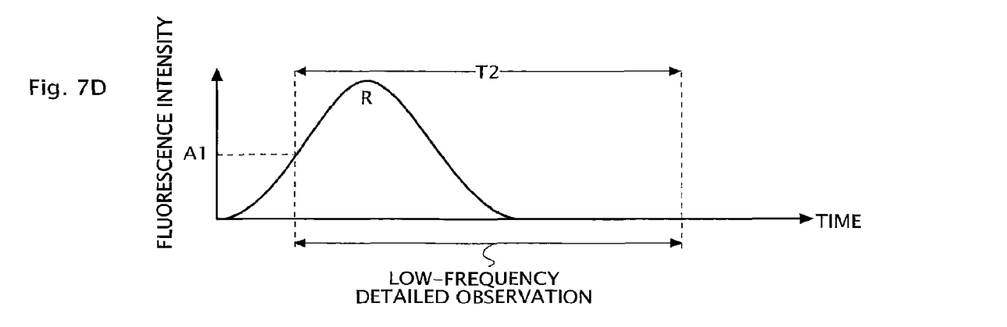

Further, the controlling unit 31 makes the user set a suspended period T2 to be provided from the start of the low-frequency detailed observation to an interruption thereof. The suspended period T2 is set at a period (shorter than the detailed observation period T1) necessary from the time when the DsRed is expressed at the cell colony until it is regarded that the Nanog-GFP is not expressed at the cell colony even if it is waited further more as illustrated in FIG. 7D. For example the suspended period T2 is set to be 336 h (two weeks).

Step S12: The controlling unit 31 compares the coarse observation schedule defined by the interval $\Delta T1$ and the current time and date, and thereby, discriminates whether or not a shooting time of the coarse observation comes. When it is discriminated that it comes, the controlling unit 31 transfers to step S13, and when it does not come, transfers to step S16.

Step S13: The observation controlling section 35 of the controlling unit 31 issues an instruction for the container transfer mechanism 26 to dispose the incubation container 15 at the observing unit 27. The container transfer mechanism 26 takes out the incubation container 15 from the stocker 25, and disposes it at a predetermined position on the stage 56 of the observing unit 27. Note that in the step S13 for a second time or later, the transfer of the incubation container 15 is not performed when the incubation container 15 is already disposed at the stage 56.

Subsequently, the observation controlling section 35 of the controlling unit 31 inputs the information of the magnification $m_L$ and the shot pattern $P_L$, and the shooting instruction of the coarse observation to the observing unit 27. The observing unit 27 receiving the above obtains two kinds of well images $I_P$, $I_R$ as for all of the wells by the following procedures (a) to (d).

(a) The observing unit 27 sets the magnification of the objective lens at the magnification $m_L$ (here, two times), and sets the illumination method to the diascopic illumination.

(b) The observing unit 27 drives the stage 56 and the shooting section 57 with the shot pattern $P_L$ while lighting only the LED for diascopic illumination 51 from among the above-stated four LEDs, and thereby, obtains the diascopic images (here, the diascopic images of 8×8×6 pieces) relating to all of the wells in the incubation container 15. These diascopic images are stored at the observation information storing section 33 of the controlling unit 31.

(c) The observing unit 27 switches the illumination method into the epi-illumination.

(d) The observing unit 27 drives the stage 56 and the shooting section 57 with the shot pattern $P_L$ while lighting the LED for fluorescence 53a under a state in which the detection channel is set at the red color channel, and thereby, obtains the DsRed images (here, the DsRed images of 8×8×6 pieces) relating to all of the wells in the incubation container 15. These DsRed images are stored at the observation information storing section 33 of the controlling unit 31.

Subsequently, the image analyzing section 34 of the controlling unit 31 creates the diascopic images for each well (six pieces of well images $I_P$) by connecting the diascopic images obtained from the same well with each other in an image obtaining order from among the diascopic images (here the 8×8×6 pieces of diascopic images) obtained by the procedure (b). Each of the above-stated six pieces of well images $I_P$ is stored at the observation information storing section 33 together with a number of the well (well number) which is the obtaining original of each image and the obtaining time and date of each image.

Besides, the image analyzing section 34 of the controlling unit 31 creates the DsRed images for each well (six pieces of well images $I_R$) by connecting the DsRed images obtained from the same well with each other in the image obtaining order from among the DsRed images (here the 8×8×6 pieces of DsRed images) obtained by the procedure (d). Each of the above-stated six pieces of well images $I_R$ is stored at the observation information storing section 33 together with the well number of the well which is the obtaining original of each image and the obtaining time and date of each image.

Step S14: The image analyzing section 34 of the controlling unit 31 compares each of the well images $I_R$ (six pieces of well images $I_R$) obtained at the last step S13 with the brightness threshold value A1, and searches one or plural high-brightness area(s) which exceed(s) the brightness threshold value A1 among the six pieces of well images $I_R$ as a setting destination of the ROI. The controlling unit 31 transfers to step S15 if even one high-brightness area is detected, and the controlling unit 31 transfers to step S16 if no high-brightness area is detected. Note that in the step S14 for a second time or later, the area where the ROI (or a later-described important ROI) is already set at the former step S14 is excluded from the search range among the six pieces of well images $I_R$.

Step S15: The image analyzing section 34 of the controlling unit 31 sets the ROI for each of the one or plural high-brightness area(s) detected at the step S14 by the following procedures (e) to (g).

(e) The image analyzing section 34 calculates a coordinate corresponding to a center of the high-brightness area (or a gravity center of brightness) on the well image $I_R$ to be the detection original of the high-brightness area.

(f) The image analyzing section 34 calculates a coordinate corresponding to the center of the high-brightness area on the incubation container 15 based on the coordinate calculated at the procedure (e) and the well number of the well image $I_R$.

(g) The image analyzing section 34 sets the ROI for the area with the size $S_{ROI}$ centering on the coordinate calculated at the procedure (f).

The image analyzing section 34 of the controlling unit 31 supplies information of a setting time and date for each of one or plural ROIs set on the incubation container 15, and supplies a number (ROI number) for each of the ROIs in a setting order. Note that the supply of the ROI number is performed not by each incubation container 15 but by each well of the incubation container 15, and the ROI number supplied for the first ROI of a certain well in the step S15 for a second time or later is the number subsequent to the ROI number supplied for the last ROI of the same well at the former step S15.

Step S16: The controlling unit 31 discriminates whether or not a shooting time of the low-frequency detailed observation comes by comparing a schedule of the low-frequency detailed observation defined by the interval ΔT2 and the current time and date, then transfers to step S17 when it comes, and transfers to step S23 when it does not come.

Step S17: The controlling unit 31 discriminates whether or not even one ROI is set at the incubation container 15, and transfers to step S18 when the ROI is set, and transfers to the step S23 when it is not set.

Step S18: The observation controlling section 35 of the controlling unit 31 issues an instruction for the container transfer mechanism 26 to dispose the incubation container 15 at the observing unit 27. The container transfer mechanism 26 takes out the incubation container 15 from the stocker 25, and disposes at the predetermined position on the stage 56 of the observing unit 27. Note that the transfer of the incubation container 15 is not performed when the incubation container 15 is already disposed on the stage 56.

The observation controlling section 35 of the controlling unit 31 inputs the information of the magnification $m_H$ and the shot pattern $P_H$, coordinate information of the set ROI and a shooting instruction of the low-frequency detailed observation to the observing unit 27. The observing unit 27 receiving the above obtains three kinds of ROI images $I_P'$, $I_R'$, $I_G'$ as for all of the set ROIs by the following procedures (a') to (k').

(a') The observing unit 27 sets the magnification of the objective lens at the magnification $m_H$ (here, 20 times), and sets the illumination method to the diascopic illumination.

(b') The observing unit 27 sets the coordinate of the stage 56 so that a center of the ROI positioning at an endmost among the set ROIs is on an optical axis of the objective lens 55.

(c') The observing unit 27 drives the stage 56 and the shooting section 57 with the shot pattern $P_H$ while lighting only the LED for diascopic illumination 51 from among the above-stated four LEDs, and thereby, the diascopic image (here, one piece of diascopic image) relating to the ROI is obtained. This diascopic image is stored at the observation information storing section 33 of the controlling unit 31.

(d') The observing unit 27 repeats the procedure (c') while changing the ROI disposed on the optical axis, and thereby, obtains the diascopic images relating to all of the ROIs.

(e') The observing unit 27 switches the illumination method into the epi-illumination.

(f') The observing unit 27 sets the coordinate of the stage 56 so that the center of the ROI positioning at the endmost among the set ROIs is on the optical axis of the objective lens 55.

(g') The observing unit 27 drives the stage 56 and the shooting section 57 with the shot pattern $P_H$ while lighting the LED for fluorescence 53a under a state in which the detection channel is set at the red color channel, and thereby, obtains the DsRed image (here, one piece of DsRed image) relating to the ROI. This DsRed image is stored at the observation information storing section 33 of the controlling unit 31.

(h') The observing unit 27 repeats the procedure (g') while changing the ROI disposed on the optical axis, and thereby, obtains the DsRed images relating to all of the ROIs.

(i') The observing unit 27 sets the coordinate of the stage 56 so that the center of the ROI positioning at the endmost among the set ROIs is on the optical axis of the objective lens 55.

(j') The observing unit 27 drives the stage 56 and the shooting section 57 with the shot pattern $P_H$ while lighting the LED for fluorescence 53b under a state in which the detection channel is set at the green color channel, and thereby, obtains the GFP image (here, one piece of GFP image) relating to the ROI. This GFP image is stored at the observation information storing section 33 of the controlling unit 31.

(k') The observing unit 27 repeats the procedure (j') while changing the ROI disposed on the optical axis, and thereby, obtains the GFP images relating to all of the ROIs.

Subsequently, the image analyzing section 34 of the controlling unit 31 creates the diascopic image (ROI image $I_F'$) for each ROI by connecting the images obtained from the same ROI with each other in the image obtaining order from among the diascopic images obtained by the procedures (b') to (d') (note that here, the number of diascopic image relating to one ROI is one piece, and therefore, the diascopic image is set to be the ROI image $I_F'$ as it is without performing the connection). Each of the created ROI images $I_F'$ is stored at the observation information storing section 33 together with the ROI number of the ROI which is the obtaining original of each image and the obtaining time and date of each image.

Besides, the image analyzing section 34 of the controlling unit 31 creates the DsRed image (ROI image $I_R'$) for each ROI by connecting the images obtained from the same ROI with each other in the image obtaining order from among the DsRed images obtained by the procedures (f') to (h') (note that here, the number of DsRed image relating to one ROI is one piece, and therefore, the DsRed image is set to be the ROI image $I_R'$ as it is without performing the connection). Each of the created ROI images $I_R'$ is stored at the observation information storing section 33 together with the ROI number of the ROI which is the obtaining original of each image and the obtaining time and date of each image.

Besides, the image analyzing section 34 of the controlling unit 31 creates the GFP image (ROI image $I_G'$) for each ROI by connecting the images obtained from the same ROI with each other in the image obtaining order from among the GFP images obtained by the procedures (i') to (k') (note that here, the number of GFP image relating to one ROI is one piece, and therefore, the GFP image is set to be the ROI image $I_G'$ as it is without performing the connection). Each of the created ROI images $I_G'$ is stored at the observation information storing section 33 together with the ROI number of the ROI which is the obtaining original of each image and the obtaining time and date of each image.

Step S19: The image analyzing section 34 of the controlling unit 31 compares a brightness average value of one or plural ROI image(s) $I_G'$ obtained at the last step S18 with the brightness threshold value A2, and thereby, finds the one which is brighter than the brightness threshold value A2 (high-brightness ROI) from among the set ROIs. When even one high-brightness ROI is found, the controlling unit 31 transfers to step S20, and the controlling unit 31 transfers to the step S23 when no high-brightness ROI is found.

Step S20: The image analyzing section 34 of the controlling unit 31 transfers the one or plural high-brightness ROI(s) found at the step S19 to important ROI(s). Note that the important ROI is an area to be an object of the high-frequency detailed observation (hereinafter, a mere ROI is referred to as an "unimportant ROI" to distinguish it from the important ROI). Besides, the image analyzing section 34 supplies information of a transferred time and date for the important ROI which is transferred from the unimportant ROI to the important ROI in this step.

Step S21: The image analyzing section 34 of the controlling unit 31 compares each of setting times and dates (the time and date when the ROI is first set to be the unimportant ROI) of all of the unimportant ROIs with the current time and date, and thereby, finds the unimportant ROI in which the suspended period T2 elapses since the setting time and date (expired ROI). When even one expired ROI is found, the controlling unit 31 transfers to step S22, and the controlling unit 31 transfers to the step S23 when no expired ROI is found.

Step S22: The image analyzing section 34 of the controlling unit 31 eliminates one or plural expired ROI(s) found at the step S21.

Step S23: The controlling unit 31 compares a schedule of the high-frequency detailed observation defined by the interval $\Delta T3$ and the current time and date to thereby discriminate whether or not a shooting time of the high-frequency detailed observation comes. The controlling unit 31 transfers to step S24 when it comes and transfers to step S28 when it does not come.

Step S24: The controlling unit 31 discriminates whether or not even one important ROI is set at the incubation container 15. The controlling unit 31 transfers to step S25 when it is set, and transfers to the step S28 when it is not set.

Step S25: The observation controlling section 35 of the controlling unit 31 issues an instruction for the container transfer mechanism 26 to dispose the incubation container 15 at the observing unit 27. The container transfer mechanism 26 takes out the incubation container 15 from the stocker 25, and disposes at the predetermined position on the stage 56 of the observing unit 27. Note that when the incubation container 15 is already disposed at the stage 56, the transfer of the incubation container 15 is not performed.

The observation controlling section 35 of the controlling unit 31 inputs the information of the magnification $m_H$ and the shot pattern $P_H$, coordinate information of a set important ROI, and the shooting instruction of the high-frequency detailed observation to the observing unit 27. The observing unit 27 receiving the above obtains three kinds of ROI images $I_F'$, $I_R'$, $I_G'$ as for all of the set important ROIs by the following procedures (a'') to (k'').

(a'') The observing unit 27 sets the magnification of the objective lens at the magnification $m_H$ (here, 20 times), and sets the illumination method to the diascopic illumination.

(b'') The observing unit 27 sets the coordinate of the stage 56 so that a center of the important ROI positioning at an endmost among the set important ROIs is on the optical axis of the objective lens 55.

(c'') The observing unit 27 drives the stage 56 and the shooting section 57 with the shot pattern $P_H$ while lighting only the LED for diascopic illumination 51 from among the above-stated four LEDs, and thereby, obtains the diascopic image (here, one piece of diascopic image) relating to the important ROI. This diascopic image is stored at the observation information storing section 33 of the controlling unit 31.

(d'') The observing unit 27 repeats the procedure (c'') while changing the important ROI disposed on the optical axis, and thereby, obtains the diascopic images relating to all of the important ROIs.

(e″) The observing unit 27 switches the illumination method to the epi-illumination.

(f″) The observing unit 27 sets the coordinate of the stage 56 so that the center of the important ROI positioning at the endmost among the set important ROIs is on the optical axis of the objective lens 55.

(g″) The observing unit 27 drives the stage 56 and the shooting section 57 with the shot pattern $P_H$ while lighting the LED for fluorescence 53a under a state in which the detection channel is set at the red color channel, and thereby, obtains the DsRed image (here, one piece of DsRed image) relating to the important ROI. This DsRed image is stored at the observation information storing section 33 of the controlling unit 31.

(h″) The observing unit 27 repeats the procedure (g″) while changing the important ROI disposed on the optical axis, and thereby, obtains the DsRed images relating to all of the important ROIs (i″) The observing unit 27 sets the coordinate of the stage 56 so that the center of the important ROI positioning at the endmost among the set important ROIs is on the optical axis of the objective lens 55.

(j″) The observing unit 27 drives the stage 56 and the shooting section 57 with the shot pattern $P_H$ while lighting the LED for fluorescence 53b under a state in which the detection channel is set at the green color channel, and thereby, obtains the GFP image (here, one piece of GFP image) relating to the important ROI. This GFP image is stored at the observation information storing section 33 of the controlling unit 31.

(k″) The observing unit 27 repeats the procedure (j″) while changing the important ROI disposed on the optical axis, and thereby, obtains the GFP images relating to all of the important ROIs.

Subsequently, the image analyzing section 34 of the controlling unit 31 creates the diascopic image (ROI image $I_P'$) for each important ROI by connecting the images obtained from the same important ROI with each other in the image obtaining order from among the diascopic images obtained by the procedures (b″) to (d″) (note that here, the number of diascopic images relating to one important ROI is one piece, and therefore, the diascopic image is set to be the ROI image $I_P'$ as it is without performing the connection). Each of the created ROI images $I_P'$ is stored at the observation information storing section 33 together with the ROI number of the important ROI which is the obtaining original of each image and the obtaining time and date of each image.

Besides, the image analyzing section 34 of the controlling unit 31 creates the DsRed image (ROI image $I_R'$) for each important ROI by connecting the images obtained from the same important ROI in the image obtaining order from among the DsRed images obtained by the procedures (f″) to (h″) (note that here, the number of DsRed images relating to one important ROI is one piece, and therefore, the DsRed image is set to be the ROI image $I_R'$ as it is without performing the connection). Each of the above-stated ROI images $I_R'$ is stored at the observation information storing section 33 together with the ROI number of the important ROI which is the obtaining original of each image and the obtaining time and date of each image.

Besides, the image analyzing section 34 of the controlling unit 31 creates the GFP image (ROI image $I_G'$) for each important ROI by connecting the images obtained from the same important ROI with each other in the image obtaining order from among the GFP images obtained by the procedures (i″) to (k″) (note that here, the number of GFP images relating to one important ROI is one piece, and therefore, the GFP image is set to be the ROI image $I_G'$ as it is without performing the connection). Each of the created ROI images $I_G'$ is stored at the observation information storing section 33 together with the ROI number of the important ROI which is the obtaining original of each image and the obtaining time and date of each image.

Step S26: The image analyzing section 34 of the controlling unit 31 compares each of the set dates and hours of all of the important ROIs (the time and date when the ROI is first set to be the important ROI) with the current time and date, and thereby, finds the important ROI in which an elapsed time since the setting time and date exceeds the detailed observation period T1 elapses (already observed ROI). When even one already observed ROI is found, the controlling unit 31 transfers to step S27, and the controlling unit 31 transfers to the step S28 when no already observed ROI is found.

Step S27: The image analyzing section 34 of the controlling unit 31 eliminates one or plural already observed ROI(s) found at the step S26.

Step S28: The controlling unit 31 issues an instruction for the container transfer mechanism 26 to house the incubation container 15 into the stocker 25. The container transfer mechanism 26 takes out the incubation container 15 from the observing unit 27, and houses it at a predetermined position of the stocker 25. Note that the transfer of the incubation container 15 is not performed when the incubation container 15 is already housed in the stocker 25 at that time.

Step S29: The controlling unit 31 discriminates whether or not a certain period (suspended period T3) elapses since any one of the important ROIs and the unimportant ROIs is not set on the incubation container 15. When the certain period elapses, the controlling unit 31 finishes the flow, and returns to the step S12 if it does not elapse. Note that when the unimportant ROI has never set on the incubation container 15, the controlling unit 31 does not perform the discrimination, and returns to the step S12 (hereinabove is the description of the flow).

Figure 6:
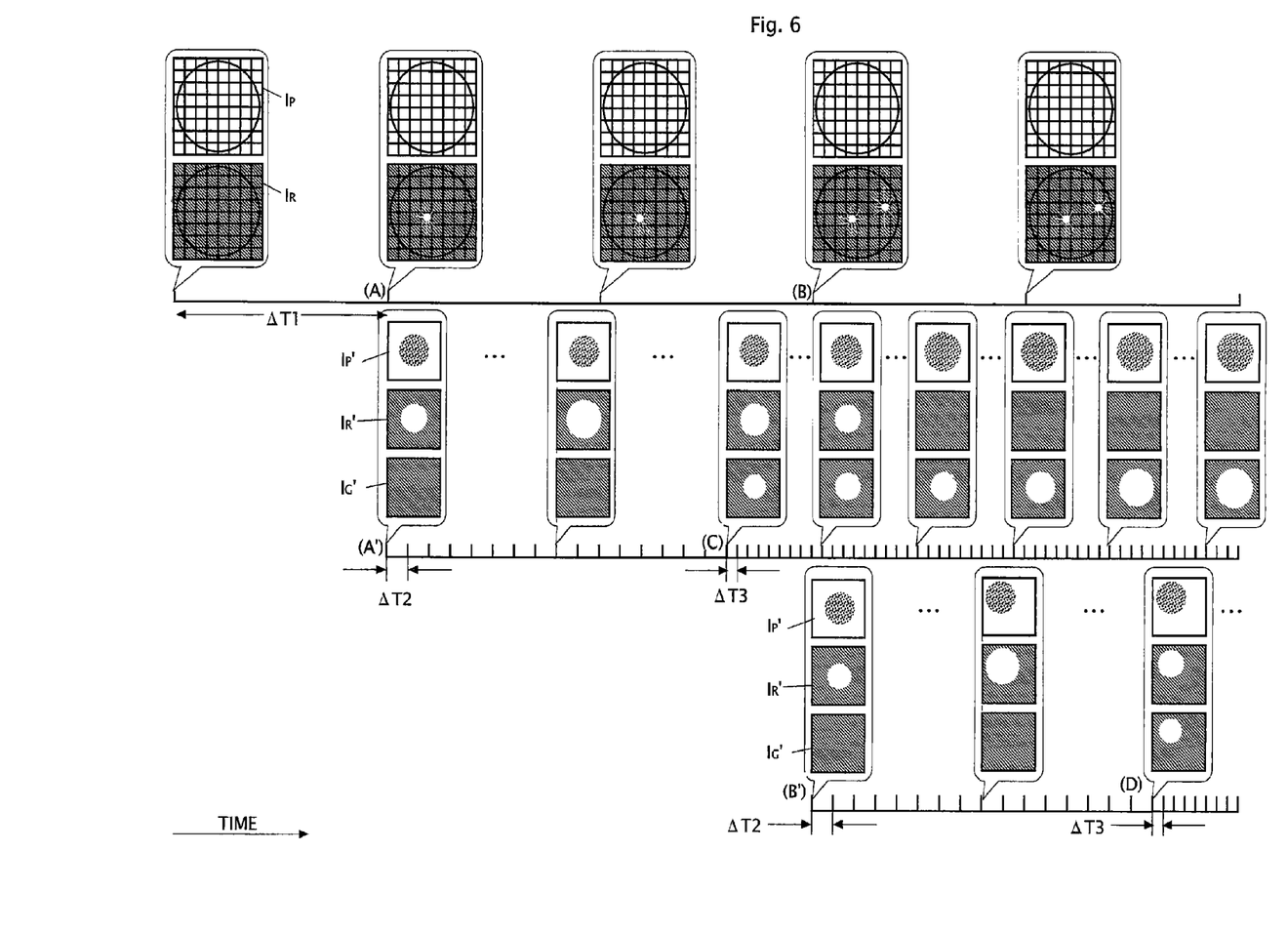
FIG. 6 is a timing chart representing an obtaining timing of each image in the observation process.

FIG. 6 is a timing chart representing an obtaining timing of each image in the above-stated observation process. Note that only an image of a certain well of the incubation container 15 is focused for easy to understanding in FIG. 6.

When the observation process is started, at first, the coarse observation is started as represented at an upper part in FIG. 6. The images obtained in respective rounds of the coarse observation are two kinds of the well images $I_P$, $I_R$, and the interval of the coarse observation is the relatively long interval ΔT1.

After that, when a high-brightness area exceeding the brightness threshold value A1 is expressed in the well image $I_R$ obtained by the coarse observation, the unimportant ROI (first unimportant ROI) is set at the area, as illustrated in FIG. 6(A).

Subsequently, when another high-brightness area exceeding the brightness threshold value A1 is expressed in the well image $I_R$ obtained by the coarse observation, the unimportant ROI (second unimportant ROI) is set at the area, as illustrated in FIG. 6(B).

Besides, when the first unimportant ROI is set (FIG. 6(A)), the low-frequency detailed observation relating to the first unimportant ROI is started as illustrated in FIG. 6(A′).

Further, when the second unimportant ROI is set (FIG. 6(B)), the low-frequency detailed observation relating to the second unimportant ROI is started as illustrated in FIG. 6(B′).

The images obtained by respective rounds of the low-frequency observation are three kinds of ROI images $I_P$, $I_R$, $I_G$, and the interval of the low-frequency detailed observation is the short interval $\Delta T2$.

When an average brightness of the ROI image $I_G{}'$ obtained by the low-frequency detailed observation of the first unimportant ROI exceeds the brightness threshold value A2, the first unimportant ROI transfers to the important ROI as illustrated in FIG. 6(C).

Besides, when an average brightness of the ROI image $I_G{}'$ obtained by the low-frequency detailed observation of the second unimportant ROI exceeds the brightness threshold value A2, the second unimportant ROI transfers to the important ROI as illustrated in FIG. 6(D).

When the first unimportant ROI transfers to the important ROI (FIG. 6(C)), the high-frequency detailed observation relating to the important ROI is started.

Besides, when the second unimportant ROI transfers to the important ROI (FIG. 6(D)), the high-frequency detailed observation relating to the important ROI is started.

The images obtained by respective rounds of the high-frequency observation are three kinds of ROI images $I_P$, $I_R$, $I_G$, and the interval of the high-frequency detailed observation is the further short interval $\Delta T3$.

Namely, the living sample observing apparatus according to the present embodiment performs the coarse observation of the whole well, and then starts the low-frequency detailed observation of a cell colony at the time when the cell colony having high possibility to be the iPS cell colony is generated in the well. The low-frequency detailed observation is transferred to the high-frequency detailed observation at the time when the possibility in which the cell colony being the object of the low-frequency detailed observation becomes the iPS cell colony is further increased.

FIGS. 7A to 7D are views representing time changes of fluorescence intensities of four cell colonies being the objects of the detailed observation in the above-stated observation process. Note that in FIGS. 7A to 7D, a reference symbol "R" represents the fluorescence intensity of the DsRed, and a reference symbol "G" represents the fluorescence intensity of the Nanog-GFP.

The time change represented in FIG. 7A relates to the cell colony in which the silencing occurs after the DsRed is expressed, and the Nanog-GFP is expressed to be the iPS cell colony before the expression of the DsRed completely terminates.

Besides, the time change represented in FIG. 7B relates to the cell colony in which the silencing occurs after the DsRed is expressed, and the Nanog-GFP is expressed to be the iPS cell colony after the expression of the DsRed terminates.

Besides, the time change represented in FIG. 7C relates to the cell colony in which the silencing occurs after the DsRed is expressed, and the Nanog-GFP is expressed after the expression of the DsRed terminates, but after that, the cell colony does not become the iPS cell colony because the expression of the Nanog-GFP terminates for some reason.

Further, the time change represented in FIG. 7D relates to the cell colony in which the silencing occurs after the DsRed is expressed, but the cell colony does not become the iPS cell colony because the Nanog-GFP is not expressed for some reason.

Among the above, the low-frequency detailed observation is started at the time when the fluorescence intensity of the DsRed exceeds the brightness threshold value A1, transfers to the high-frequency detailed observation when the fluorescence intensity of the Nanog-GFP exceeds the brightness threshold value A2, and the detailed observation finishes at the time when the detailed observation period T1 elapses since the start time of the low-frequency detailed observation as for the cell colonies in which both of the DsRed and the Nanog-GFP are expressed (FIGS. 7A to 7C).

Accordingly, the time change of the fluorescence intensity of the DsRed and the time change of the fluorescence intensity of the Nanog-GFP are each imaged at a proper frequency and for a proper period as for the cell colonies in which both of the DsRed and the Nanog-GFP are expressed (FIGS. 7A to 7C).

On the other hand, the low-frequency detailed observation is started at the time when the fluorescence intensity of the DsRed exceeds the brightness threshold value A1, and the detailed observation is interrupted at the time when the suspended period T2 elapses since the start time thereof as for the cell colony in which only the former one is expressed between the DsRed and the Nanog-GFP (FIG. 7D).

Accordingly, only the time change of the fluorescence intensity of the DsRed is imaged at the proper frequency and for the proper period as for the cell colony in which only the former one is expressed between the DsRed and the Nanog-GFP (FIG. 7D).

Namely, the living sample observing apparatus according to the present embodiment images respective states of various cell colonies each at the proper frequency and for the proper period.

As a result, the living sample observing apparatus according to the present embodiment is able to effectively observe the iPS cell colony irregularly expressed at the incubation container 15.

Here, it is necessary to irradiate excitation light to perform the fluorescence observation of the cells at the incubation container 15, and an irradiation amount of the excitation light is to be suppressed as much as possible because the fluorescence observation involves damages on the cells. Accordingly, the present embodiment in which the timing, the frequency, and so on observing a narrow range of the incubation container 15 in detail (perform a micro observation) are appropriately set in accordance with the states of the cells is effective to suppress the damages on the cells.

Further, there is a possibility in which self-fluorescence from the cell colony disturbs the observation of an object colony when a wide range of the incubation container 15 is coarsely observed (perform a macro observation), and therefore, the present embodiment appropriately performing the micro observation is effective.

[Supplementary Items of the Embodiments]

Figure 8:
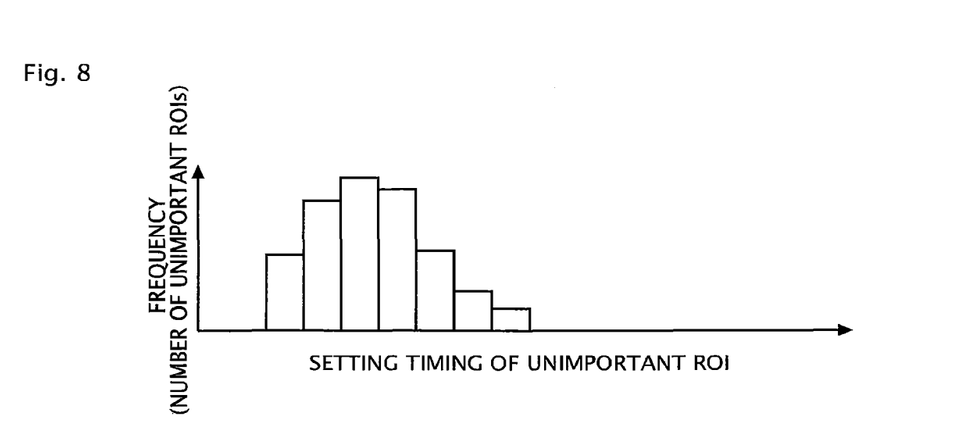
FIG. 8 is a graphic chart representing a relationship between a setting timing of an unimportant ROI and the number of unimportant ROIs.

Note that the controlling unit 31 of the above-stated embodiment may create, for each well or for each incubation container, a histogram representing a relationship between the setting timing of the unimportant ROI and the number of set unimportant ROIs as, for example, represented in FIG. 8, and stores the histogram to the observation information storing section 33 after the observation process illustrated in FIG. 5 finishes or during the execution process of the observation process. This histogram is a histogram of the expression timing of the DsRed.

Figure 9:
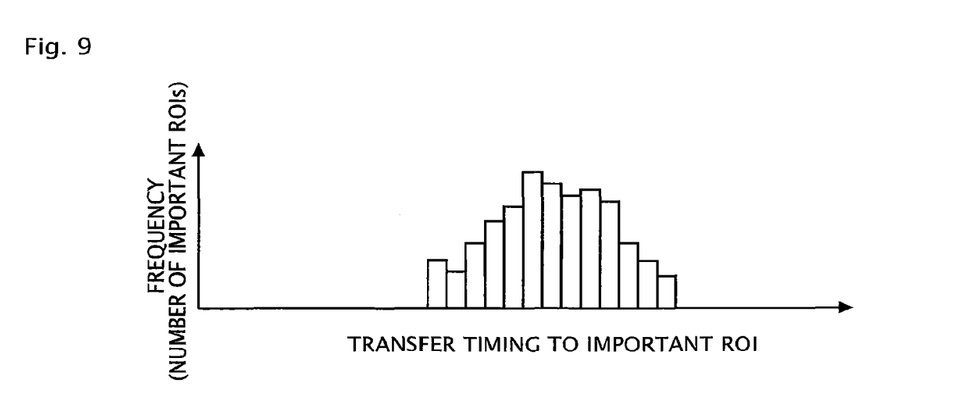
FIG. 9 is a graphic chart representing a relationship between a transition timing of an important ROI and the number of important ROIs.

Besides, the controlling unit 31 of the above-stated embodiment may create, for each well or for each incubation container, a histogram representing a relationship between a transfer timing of the important ROI (the transfer timing from the unimportant ROI to the important ROI) and the number of important ROIs as, for example, represented in FIG. 9, and stores the histogram to the observation information storing section 33 after the observation process illustrated in FIG. 5 finishes or during the execution process of the observation process. This histogram is a histogram of the expression timing of the Nanog-GFP.

Further, the controlling unit 31 of the above-stated embodiment may create a time lapse moving image (a time lapse moving image of the DsRed) by each ROI number by connecting the plural ROI images $I_R$ (the ROI image $I_R$ of the unimportant ROI and the ROI image $I_R$ of the important ROI) of which ROI number is in common in the image obtaining order, and stores the image to the observation information storing section 33 after the observation process illustrated in FIG. 5 finishes or during the execution process of the observation process. Note that the interval of the ROI image $I_R$ of the unimportant ROI if wider than that of the ROI image $I_R$ of the important ROI, and therefore, it is desirable to interpolate the ROI image $I_R$ of the unimportant ROI in a time direction when both of them are connected.

Similarly, the controlling unit 31 of the above-stated embodiment may create a time lapse moving image (a time lapse moving image of the Nanog-GFP) by each ROI number by connecting the plural ROI images $I_G$ (the ROI image $I_G$ of the unimportant ROI and the ROI image $I_G$ of the important ROI) of which ROI number is in common in the image obtaining order, and stores the image to the observation information storing section 33 after the observation process illustrated in FIG. 5 finishes or during the execution process of the observation process. Note that the interval of the ROI image $I_G$ of the unimportant ROI if wider than that of the ROI image $I_G$ of the important ROI, and therefore, it is desirable to interpolate the ROI image $I_G$ of the unimportant ROI in the time direction when both of them are connected.

Similarly, the controlling unit 31 of the above-stated embodiment may create a time lapse moving image (a time lapse moving image of the diascopic image) by each ROI number by connecting the plural ROI images $I_P$ (the ROI image IP of the unimportant ROI and the ROI image $I_P$ of the important ROI) of which ROI number is in common in the image obtaining order, and stores the image to the observation information storing section 33 after the observation process illustrated in FIG. 5 finishes or during the execution process of the observation process. Note that the interval of the ROI image $I_P$ of the unimportant ROI if wider than that of the ROI image $I_P$ of the important ROI, and therefore, it is desirable to interpolate the ROI image $I_P$ of the unimportant ROI in the time direction when both of them are connected.

Further, the controlling unit 31 of the above-stated embodiment may automatically discriminate whether or not the cell colony taken in the time lapse moving images is the iPS cell colony based on the DsRed time lapse moving image and the Nanog-GFP time lapse moving image of which ROI number is in common.

For example, the controlling unit 31 may compare a latest frame of the DsRed time lapse moving image and a latest frame of the Nanog-GFP time lapse moving image, and regards that the cell colonies taken in the time lapse moving images are the iPS cell colonies when the latter one is larger than the former one for a certain degree or more, and otherwise, regards that the cell colonies taken in the time lapse moving images are non-iPS cell colonies.

According to the discrimination method as stated above, it is possible to determine that the cell colonies going through the fluorescence intensity change as illustrated in FIGS. 7A and 7B are the iPS cell colonies, and the cell colonies going through the fluorescence intensity change as illustrated in FIGS. 7C and 7D are the non-iPS cell colonies.

Besides, in the above-stated embodiment, the incubation container 15 is assumed to be the well plate, but it may be the other incubation containers such as a dish and a flask.

The many features and advantages of the embodiment are apparent from the detailed specification and, thus, it is intended by the appended claims to cover all such features and advantages of the embodiment that fall within the true spirit and scope thereof. Further, since numerous modifications and changes will readily occur to those skilled in the art, it is not desired to limit the inventive embodiment to the exact construction and operation illustrated and described, and accordingly all suitable modifications and equivalents may be resorted to, falling within the scope thereof.

What is claimed is:

1. An observing apparatus, comprising:
an image-forming optical system and an imaging device configured to perform a first time lapse shooting of a first observation area at a first shooting frequency and a second time lapse shooting of a second observation area at a second shooting frequency that is higher than the first shooting frequency;
a controller configured to determine whether or not a first material is expressed in the first observation area based on an image obtained during the first time lapse shooting and, when the first material is expressed in the first observation area, to control the image-forming optical system and the imaging device to begin performing the second time lapse shooting of the second observation area at a time when the first material is expressed in the first observation area, the second observation area being an area within the first observation area in which the first material is expressed.

2. The observing apparatus according to claim 1, wherein the controller is configured to determine whether or not a second material different from the first material is expressed in the second observation area, and
when the second material is expressed in the second observation area, to control the image-forming optical system and the imaging device to increase the second shooting frequency of the second time lapse shooting, at a timing when the second material is expressed in the second observation area.

3. The observing apparatus according to claim 2, wherein the controller is configured to set an end timing of the second time lapse shooting at a point in time when a predetermined time elapsed since the first material is expressed.

4. The observing apparatus according to claim 2, wherein the controller is configured to interrupt the second time lapse shooting when the second material is not expressed after a predetermined time elapses since the first material is expressed.

5. The observing apparatus according to claim 2, wherein both of a first image to observe the first material and a second image to observe the second material are obtained in each round of the second time lapse shooting, and
only a former of the first image and the second image is obtained in each round of the first time lapse shooting.

6. The observing apparatus according to claim 2, wherein when the first material is expressed at a plurality of parts different from one another in the first observation area at different timings, the second time lapse shooting relating to each of the plurality of parts is started at each expression timing.

7. The observing apparatus according to claim 6, further comprising a statistics obtaining unit finding a relationship between an expression timing of the first material and the number of parts where the first material is expressed.

8. The observing apparatus according to claim 6, further comprising
a statistics obtaining unit finding a relationship between an expression timing of the second material and the number of parts where the second material is expressed.

9. The observing apparatus according to claim 2, further comprising:
a laser light source irradiating laser light on the first observation area; and
an imaging section detecting fluorescence being emitted from the first observation area including the first material and the second material when the first observation area is excited by the laser light, wherein
light intensity of fluorescence of the first material being detected by the imaging section is compared with a predetermined level to discriminate whether or not the first material is expressed, and
light intensity of fluorescence of the second material being detected by the imaging section is compared with a predetermined level to discriminate whether or not the second material is expressed.

10. The observing apparatus according to claim 1, wherein
the first observation area is all or a part of an area of an incubation container incubating a living sample, and
the observing apparatus further comprises an environmental controlling unit controlling an environment of the incubation container.

11. The observing apparatus according to claim 1, wherein determining whether or not the first material is expressed in the first observation area is a determination whether or not the first material is first-ever expressed, without previously having been expressed, in the first observation area.

12. An observation method, comprising:
performing a first time lapse shooting of a first observation area at a first shooting frequency;
performing a second time lapse shooting of a second observation area at a second shooting frequency that is higher than the first shooting frequency;
determining whether or not a first material is expressed in the first observation area based on an image obtained during the first time lapse shooting; and
beginning to perform, when the first material is expressed in the first observation area, the second time lapse shooting of the second observation area at a time when the first material is expressed in the first observation area, the second observation area being an area within the first observation area in which the first material is expressed.

13. The observation method according to claim 12, further comprising:
determining whether or not a second material different from the first material is expressed in the second observation area; and
increasing the second shooting frequency of the second time lapse shooting at a timing when the second material is expressed.

14. The observation method according to claim 13, further comprising:
irradiating laser light at the first observation area; and
detecting fluorescence being emitted by the first observation area including the first material and the second material when the first observation area is excited by the laser light, wherein
determining whether or not a first material is expressed in the first observation area compares light intensity of fluorescence of the first material being detected by said detecting with a predetermined level to determine whether or not the first material is expressed, and
determining whether or not a second material different from the first material is expressed compares light intensity of fluorescence of the second material being detected by said detecting with a predetermined level to determine whether or not the second material is expressed.

15. The observing method according to claim 12, wherein the determining whether or not the first material is expressed in the first observation area is a determination whether or not the first material is first-ever expressed, without previously having been expressed, in the observation area.

* * * * *

UNITED STATES PATENT AND TRADEMARK OFFICE
CERTIFICATE OF CORRECTION

PATENT NO. : 9,927,605 B2
APPLICATION NO. : 13/565281
DATED : March 27, 2018
INVENTOR(S) : Hiroaki Kii Page 1 of 1

It is certified that error appears in the above-identified patent and that said Letters Patent is hereby corrected as shown below:

In the Claims

Column 20, Line 38:
In Claim 15, delete "observing" and insert -- observation -- therefore.

Signed and Sealed this
Thirty-first Day of July, 2018

Andrei Iancu
*Director of the United States Patent and Trademark Office*